(12) United States Patent
Lewis-Williams

(10) Patent No.: US 9,003,571 B1
(45) Date of Patent: Apr. 14, 2015

(54) PANTIES WITH STORAGE COVERS

(71) Applicant: Sonya D. Lewis-Williams, Baton Rouge, LA (US)

(72) Inventor: Sonya D. Lewis-Williams, Baton Rouge, LA (US)

( * ) Notice: Subject to any disclaimer, the term of this patent is extended or adjusted under 35 U.S.C. 154(b) by 190 days.

(21) Appl. No.: 13/719,922

(22) Filed: Dec. 19, 2012

(51) Int. Cl.
*A41B 9/04* (2006.01)

(52) U.S. Cl.
CPC ........................................ *A41B 9/04* (2013.01)

(58) Field of Classification Search
CPC ............ A41B 9/08; A41B 9/001; A41B 9/04; A41D 27/20
USPC ........................... 604/393, 395, 396, 398, 400
See application file for complete search history.

(56) References Cited

U.S. PATENT DOCUMENTS

| | | | |
|---|---|---|---|
| 2,028,007 A * | 1/1936 | Pecknold | 604/398 |
| 2,039,446 A * | 5/1936 | Pecknold | 604/398 |
| 2,102,359 A * | 12/1937 | Frieman | 604/396 |
| 2,977,957 A * | 4/1961 | Clyne | 604/396 |
| 3,424,162 A | 1/1969 | Parravicini | |
| 3,599,638 A | 8/1971 | Rickard | |
| 4,035,844 A * | 7/1977 | Atack et al. | 2/466 |
| 4,044,769 A * | 8/1977 | Papajohn | 604/396 |
| 4,067,068 A * | 1/1978 | Bregstein et al. | 2/406 |
| 4,351,340 A | 9/1982 | McLeod | |
| 4,352,356 A * | 10/1982 | Tong | 604/402 |
| 4,560,381 A * | 12/1985 | Southwell | 604/396 |
| 5,062,839 A | 11/1991 | Anderson | |
| 5,067,178 A * | 11/1991 | Katchka | 2/250 |
| D330,590 S | 10/1992 | Pressley et al. | |
| 5,539,926 A * | 7/1996 | Mantos | 2/23 |
| 5,819,323 A * | 10/1998 | Edenfield | 2/466 |
| 6,240,569 B1 | 6/2001 | Van Gompel et al. | |
| D447,808 S * | 9/2001 | Ross | D24/206 |
| 8,123,735 B2 * | 2/2012 | Deerin | 604/396 |
| 2006/0101558 A1* | 5/2006 | Coleman et al. | 2/400 |
| 2007/0021727 A1* | 1/2007 | Fabrega et al. | 604/385.19 |

* cited by examiner

*Primary Examiner* — Amy Vanatta
*Assistant Examiner* — Sally Haden

(57) ABSTRACT

The present invention features a panties system with built-in storage covers for sanitary pad. The panties include an elastic waistband, a front panel and a back panel, a crotch panel to cover the genital area, a pair of leg openings. The crotch panel has a first crotch cover and a second crotch cover. The covers are adjacent to each other and sewed to the leg openings. The covers have optional elastic edges to hold sanitary pads on position securely between the crotch panel and crotch covers.

8 Claims, 5 Drawing Sheets

PANTIES WITH STORAGE COVERS

FIELD OF THE INVENTION

The present invention is related to panties, and more particularly to panties with storage covers for sanitary pad.

BACKGROUND OF THE INVENTION

Panties are a form of underwear to be worn by women and girls in the crotch area below the waist. During the period times, women and girls need to replace sanitary pad or sanitary napkin frequently and sometimes in awkward situations wherein their purses or carry-on bags are not immediately available. Therefore, there is a need for panties with built-in storage pockets for sanitary pad such that women and girls can replace sanitary pad conveniently during those awkward situations.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a panties system with built-in storage covers for sanitary pad. The panties include an elastic waistband, a front panel and a back panel, a crotch panel to cover the genital area, a pair of leg openings. The crotch panel has a first crotch cover and a second crotch cover. The covers are adjacent to each other and sewed to the leg openings. The covers have optional elastic edges to hold sanitary pads on position securely between the crotch panel and crotch covers.

DESCRIPTION OF PREFERRED EMBODIMENTS

Figure 1:
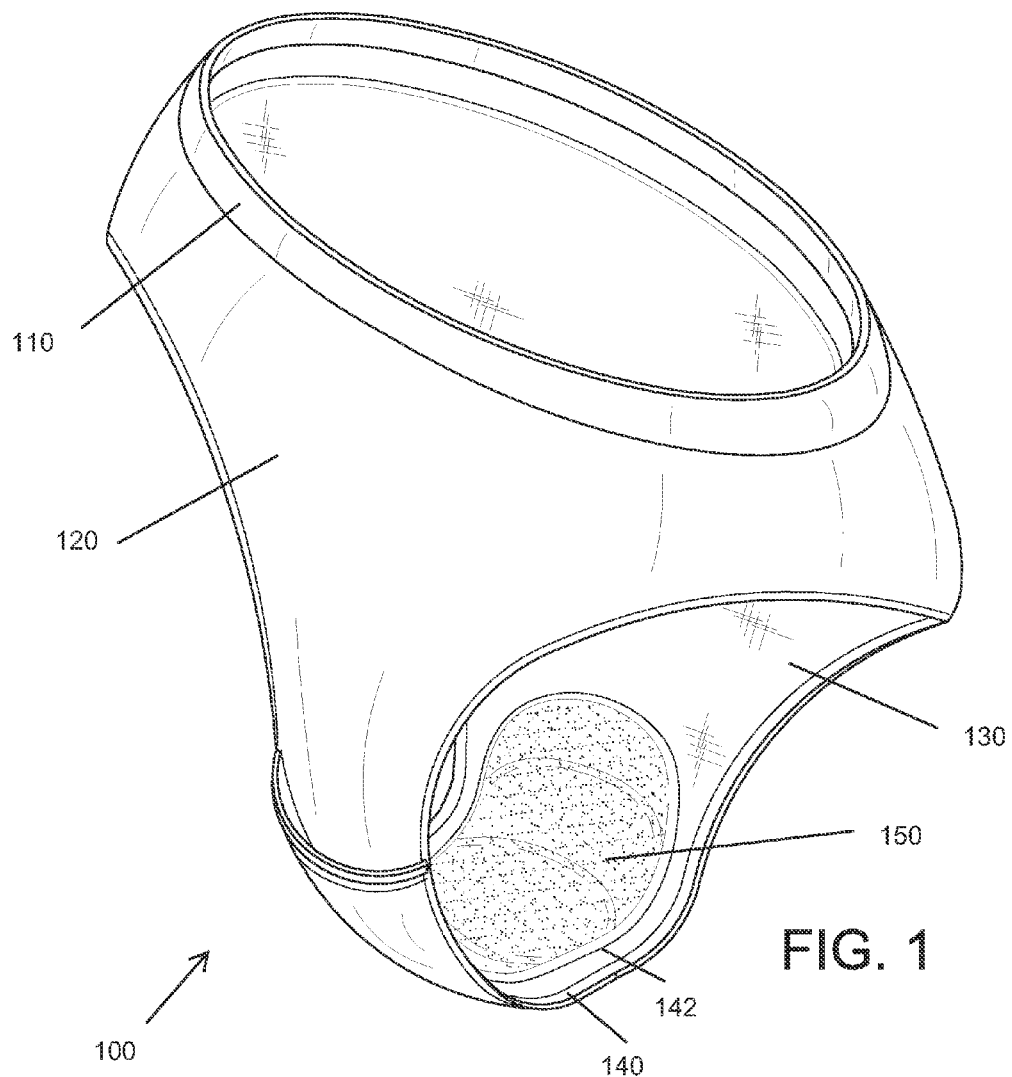
FIG. 1 shows a left isometric view of the panties.
Figure 2:
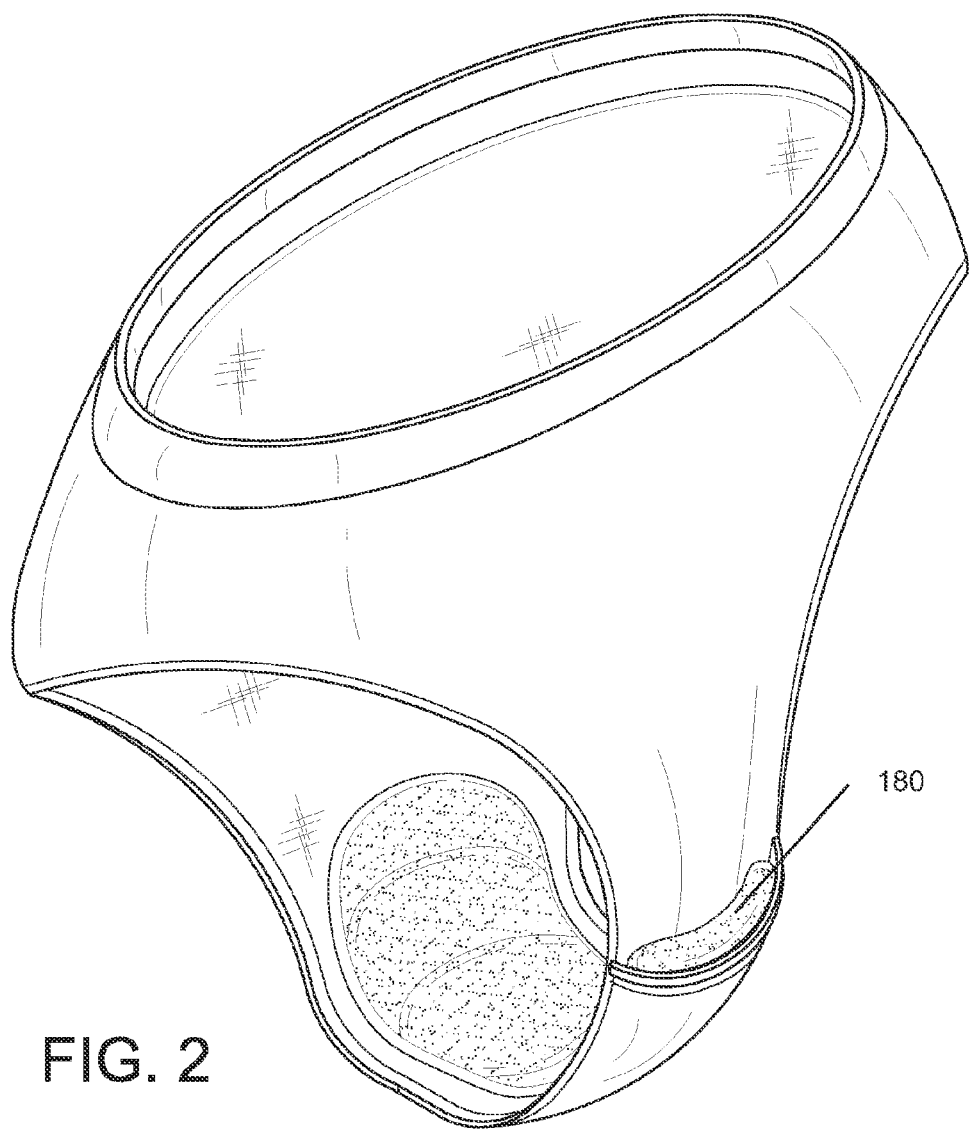
FIG. 2 shows a right isometric view of the panties.
Figure 3:
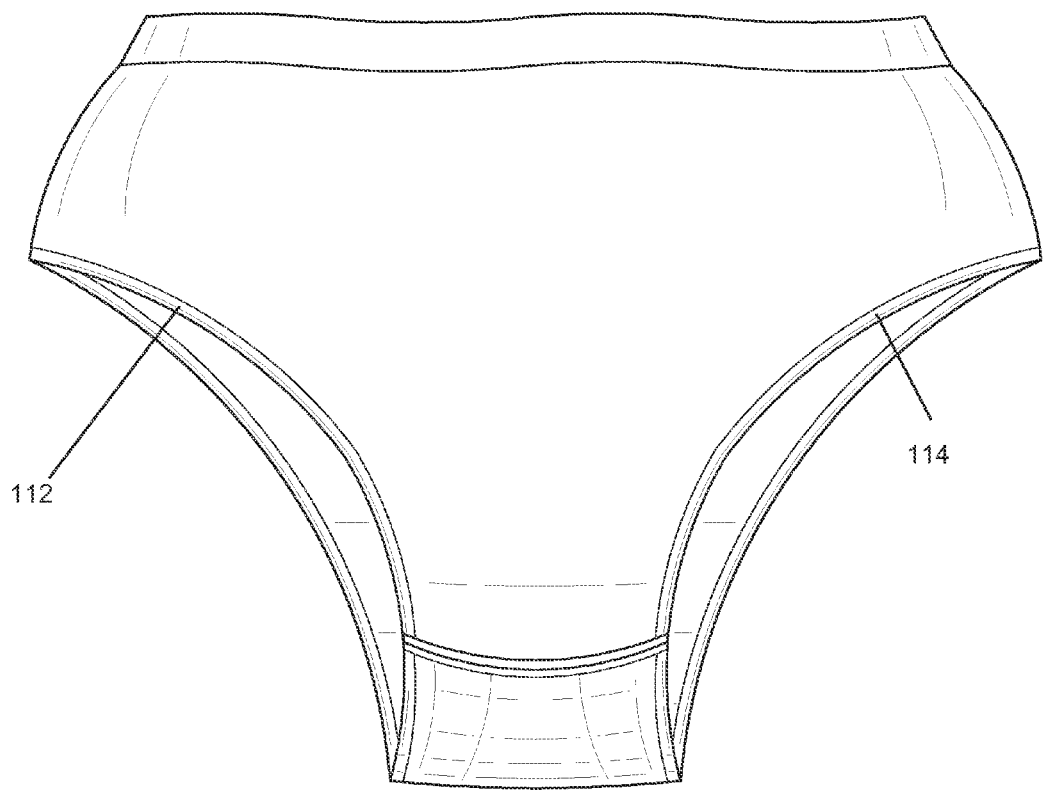
FIG. 3 shows a front view of the panties.
Figure 4:
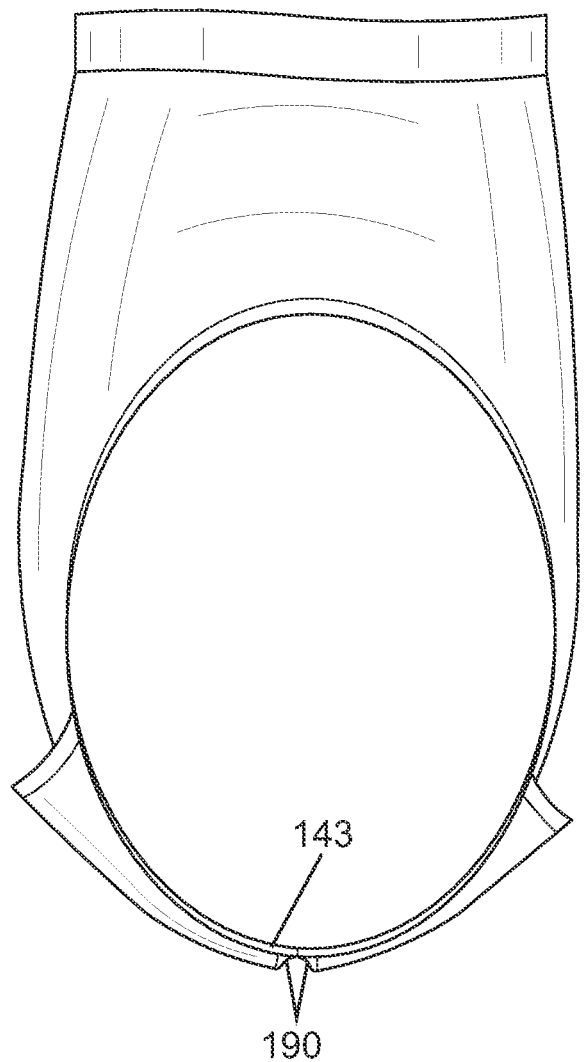
FIG. 4 shows a side view of the panties.
Figure 5:
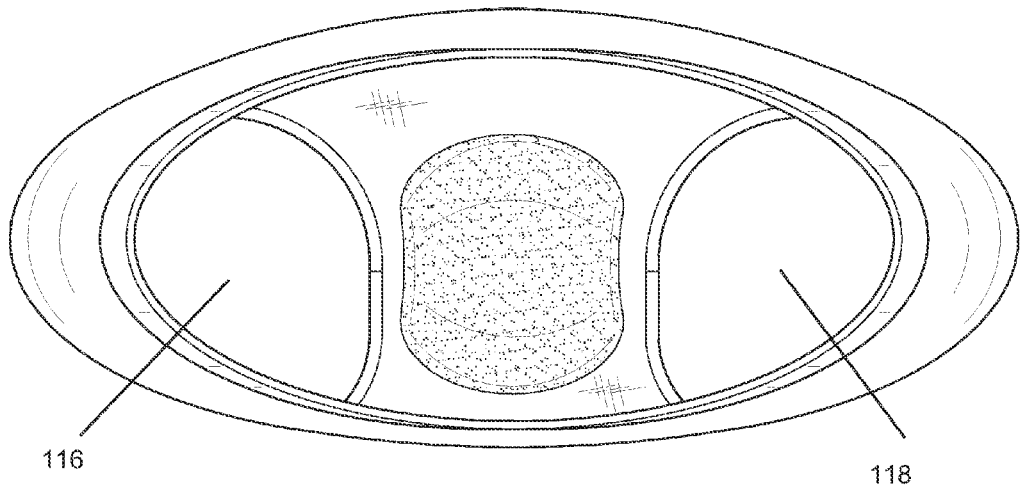
FIG. 5 shows a top view of the panties.
Figure 6:
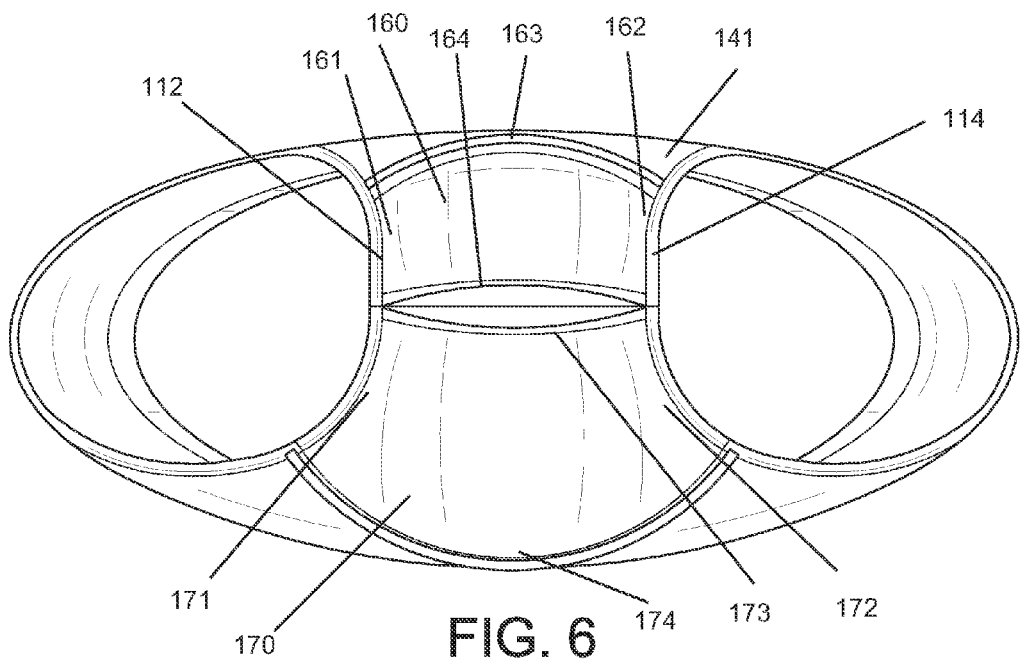
FIG. 6 shows a bottom view of the panties.

Following is a list of elements corresponding to a particular element referred to herein:

100 the panties with storage covers
110 elastic waistband
112 first leg opening edge
114 second leg opening edge
116 first leg opening
118 second leg opening
120 front panel
130 back panel
140 crotch panel
141 crotch panel outside surface
142 crotch panel inside surface
150 crotch liner
160 first crotch cover
161 first edge of first crotch cover
162 second edge of first crotch cover
163 third edge of first crotch cover
164 fourth edge of first crotch cover
170 second crotch cover
171 first edge of second crotch cover
172 second edge of second crotch cover
173 third edge of second crotch cover
174 fourth edge of second crotch cover
180 hygiene pad Referring now to FIG. 1-6, the present invention features a panties system (100) comprising an elastic waistband (110), a front panel (120) and a back panel (130), a crotch panel (140) to cover the genital area and joint the front panel (120) and back panel (130). In some embodiments, the front panel (120) and the back panel (130) are narrow straps. The panties can have the styles of classic briefs, high-cut briefs, hipster, bikinis, Tanga, or thong. In some embodiments, the front panel (120) and back panel (130) and crotch panel (140) are from single cloth/fabrics piece. In some embodiments, the front panel (120) and back panel (130) and crotch panel (140) are different cloth/fabrics pieces.

A first leg opening (116) and second leg opening (118) are disposed between the front panel (120) and the back panel (130), wherein the first leg opening (116) has a first leg opening edge (112) and the second leg opening (118) has a second leg opening edge (114), wherein the crotch panel (140) has an outside surface (141) and inside surface (142). In some embodiments, a crotch liner (150) is disposed on the inside surface (142) of the crotch panel (140), wherein the crotch liner is made with absorbent material such as cotton. In some embodiments, the first leg opening edge (112) or the second leg opening edge (114) are elastic in part or in whole length.

A first crotch cover (160) and a second crotch cover (170) disposed on the outside surface (142) of the crotch panel (140), wherein the first crotch cover (160) has a first edge (161), a second edge (162), a third edge (163) and a fourth edge (164), wherein the second crotch cover (170) has a first edge (171), a second edge (172), a third edge (173) and a fourth edge (174), wherein the first edge (161) and the second edge (162) of the first crotch cover (160) are securely attached to the crotch panel (140), wherein the third edge (163) and the fourth edge (164) of the first crotch cover (160) are free spanning, wherein the first edge (171) and the second edge (172) of the second crotch cover (170) are securely attached to the crotch panel (140), wherein the third edge (173) and the fourth edge (174) of the second crotch cover (170) are free spanning, wherein a hygiene pad (180) is insertable from the direction of the front panel (120) or the back panel (130) and reside between the outside surface (142) of the crotch panel (140) and both crotch covers. The hygiene pad (180) is a sanitary napkin, sanitary towel, sanitary pad, or a panty liner.

In some embodiments, the fourth edge (164) of the first crotch cover (160) is adjacent to the third edge (173) of the second crotch cover (170) forming an open slit (190) located towards a bottom-most region (143) of the crotch panel (140). Such gapless configuration ensures that there is no gap between the first crotch cover (160) and the second crotch cover (170) at the first (161, 171) and second (162, 172) edges of the first and second crotch covers and thus prevents the hygiene pad (180) from being contaminated by the outer layer pants. In some embodiments, the fourth edge (164) of the first crotch cover (160) is a certain distance away to the third edge (173) of the second crotch cover (170) such that there is some gap between the first crotch cover (160) and the second crotch cover (170).

In some embodiments, the first edge (161) of the first crotch cover (160) and the first edge (171) of the second crotch cover (170) are adjacent to the first leg opening edge (112), wherein the second edge (162) of the first crotch cover (160) and the second edge (172) of the second crotch cover (170) are adjacent to the second leg opening edge (114).

In some embodiments, the first edge (161) of the first crotch cover (160) and the first edge (171) of the second crotch cover (170) have margins to the first leg opening edge (112), wherein the second edge (162) of the first crotch cover (160) and the second edge (172) of the second crotch cover (170) have margins to the second leg opening edge (114).

In some embodiments, the third edge (163) or the fourth edge (164) of the first crotch cover (160) or the third edge (173) or the fourth edge (174) of the second crotch cover (170) are elastic. In some embodiments, the first crotch cover (160) or the second crotch cover (170) are made with elastic fabrics, such as spandex or elastane.

In some embodiments, the panties can have more than two crotch covers. The purpose of multiple covers is to provide assistance to a user to fully insert the hygiene pad between the crotch panel and the crotch panels. The user may grip the hygiene pad between crotch panel edges for assistance in insertion.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. A panties system with built-in storage covers, wherein the panties (100) comprise:
   (a) an elastic waistband (110);
   (b) a front panel (120), a back panel (130) and a crotch panel (140) joining the front panel (120) and back panel (130); wherein a first leg opening (116) and second leg opening (118) are disposed between the front panel (120) and the back panel (130), wherein the first leg opening (116) has a first leg opening edge (112) and the second leg opening (118) has a second leg opening edge (114), wherein the crotch panel (140) has an outside surface (141) and inside surface (142);
   (c) a first crotch cover (160) and a second crotch cover (170) disposed on the outside surface (142) of the crotch panel (140), wherein the first crotch cover (160) has a first edge (161), a second edge (162), a third edge (163) and a fourth edge (164), wherein the second crotch cover (170) has a first edge (171), a second edge (172), a third edge (173) and a fourth edge (174), wherein the first edge (161) and the second edge (162) of the first crotch cover (160) are securely attached to the crotch panel (140), wherein the third edge (163) and the fourth edge (164) of the first crotch cover (160) are free spanning, wherein the first edge (171) and the second edge (172) of the second crotch cover (170) are securely attached to the crotch panel (140), wherein the third edge (173) and the fourth edge (174) of the second crotch cover (170) are free spanning, wherein the fourth edge (164) of the first crotch cover (160) is adjacent to the third edge (173) of the second crotch cover (170) forming an open slit (190) located towards a bottom-most region (143) of the crotch panel (140), wherein there is no gap between the first crotch cover (160) and the second crotch cover (170) at the first (161, 171) and second (162, 172) edges of the first and second crotch covers, wherein a hygiene pad (180) is insertable from the direction of the front panel (120) or the back panel (130) and resides between the outside surface (142) of the crotch panel (140) and both crotch covers.

2. The panties system of claim 1, wherein the first edge (161) of the first crotch cover (160) and the first edge (171) of the second crotch cover (170) are adjacent to the first leg opening edge (112), wherein the second edge (162) of the first crotch cover (160) and the second edge (172) of the second crotch cover (170) are adjacent to the second leg opening edge (114).

3. The panties system of claim 1, wherein the first leg opening edge (112) or the second leg opening edge (114) are elastic in part or in whole length.

4. The panties system of claim 1, wherein a crotch liner (150) is disposed on the inside surface (142) of the crotch panel (140), wherein the crotch liner is made with absorbent material.

5. The panties system of claim 1, wherein the third edge (163) or the fourth edge (164) of the first crotch cover (160) or the third edge (173) or the fourth edge (174) of the second crotch cover (170) are elastic.

6. The panties system of claim 1, wherein the first crotch cover (160) or the second crotch cover (170) are made with elastic fabrics.

7. The panties system of claim 1, wherein the hygiene pad (180) is a sanitary napkin, sanitary towel, sanitary pad, or a panty liner.

8. A panties system with built-in storage covers, wherein the panties (100) consist of:
   (a) an elastic waistband (110);
   (b) a front panel (120), a back panel (130) and a crotch panel (140) joining the front panel (120) and back panel (130); wherein a first leg opening (116) and second leg opening (118) are disposed between the front panel (120) and the back panel (130), wherein the first leg opening (116) has a first leg opening edge (112) and the second leg opening (118) has a second leg opening edge (114), wherein the crotch panel (140) has an outside surface (141) and inside surface (142);
   (c) a first crotch cover (160) and a second crotch cover (170) disposed on the outside surface (142) of the crotch panel (140), wherein the first crotch cover (160) has a first edge (161), a second edge (162), a third edge (163) and a fourth edge (164), wherein the second crotch cover (170) has a first edge (171), a second edge (172), a third edge (173) and a fourth edge (174), wherein the first edge (161) and the second edge (162) of the first crotch cover (160) are securely attached to the crotch panel (140), wherein the third edge (163) and the fourth edge (164) of the first crotch cover (160) are free spanning, wherein the first edge (171) and the second edge (172) of the second crotch cover (170) are securely attached to the crotch panel (140), wherein the third edge (173) and the fourth edge (174) of the second crotch cover (170) are free spanning, wherein the fourth edge (164) of the first crotch cover (160) is adjacent to the third edge (173)

of the second crotch cover (170) forming an open slit (190) located towards a bottom-most region (143) of the crotch panel (140), wherein there is no gap between the first crotch cover (160) and the second crotch cover (170) at the first (161, 171) and second (162, 172) edges of the first and second crotch covers, wherein a hygiene pad (180) is insertable from the direction of the front panel (120) or the back panel (130) and resides between the outside surface (142) of the crotch panel (140) and both crotch covers.

* * * * *